US011547645B2

(12) United States Patent
Stebbins et al.

(10) Patent No.: US 11,547,645 B2
(45) Date of Patent: Jan. 10, 2023

(54) ORGANIC UVA FILTER-STABILIZED ANTIOXIDANT COMPOSITION

(71) Applicant: L'OREAL, Paris (FR)

(72) Inventors: Nicholas David Stebbins, Clark, NJ (US); Susan Halpern Chirch, Basking Ridge, NJ (US)

(73) Assignee: L'OREAL, Paris (FR)

( * ) Notice: Subject to any disclaimer, the term of this patent is extended or adjusted under 35 U.S.C. 154(b) by 164 days.

(21) Appl. No.: 17/141,865

(22) Filed: Jan. 5, 2021

(65) Prior Publication Data

US 2022/0211599 A1 Jul. 7, 2022

(51) Int. Cl.
| | | |
|---|---|---|
| A61K 8/34 | (2006.01) | |
| A61K 8/36 | (2006.01) | |
| A61K 8/37 | (2006.01) | |
| A61K 8/42 | (2006.01) | |
| A61K 8/46 | (2006.01) | |
| A61K 8/67 | (2006.01) | |
| A61K 8/73 | (2006.01) | |
| A61Q 1/14 | (2006.01) | |
| A61Q 19/10 | (2006.01) | |
| A61K 8/55 | (2006.01) | |

(52) U.S. Cl.
CPC .............. *A61K 8/466* (2013.01); *A61K 8/345* (2013.01); *A61K 8/36* (2013.01); *A61K 8/37* (2013.01); *A61K 8/42* (2013.01); *A61K 8/55* (2013.01); *A61K 8/676* (2013.01); *A61K 8/678* (2013.01); *A61K 8/735* (2013.01); *A61Q 1/14* (2013.01); *A61Q 19/10* (2013.01)

(58) Field of Classification Search
USPC ......................................................... 514/54
See application file for complete search history.

(56) References Cited

U.S. PATENT DOCUMENTS

| | | | | |
|---|---|---|---|---|
| 7,179,841 | B2 * | 2/2007 | Zielinski | A61K 8/676 |
| | | | | 514/474 |
| 8,268,293 | B2 * | 9/2012 | Rudolph | A61P 1/02 |
| | | | | 424/59 |
| 9,585,822 | B2 * | 3/2017 | Lewis, II | A61K 8/673 |
| 2005/0154054 | A1 | 7/2005 | Zielinski et al. | |
| 2013/0123207 | A1 | 5/2013 | Sardi | |
| 2019/0298638 | A1 | 10/2019 | Pan et al. | |

FOREIGN PATENT DOCUMENTS

| | | |
|---|---|---|
| FR | 2 932 679 A1 | 12/2009 |
| FR | 3 034 987 A1 | 10/2016 |

OTHER PUBLICATIONS

Mintel, Clarifying Carection Cream, ID 3326113, published Jul. 2015, pp. 1-5.*
Mintel, Anonymous, "AHC Natural Perfection Pro Shield—Sun Perfector SPF 50+ PA++++", Record ID 7615847, May 2020, wwww.gnpd.com.
Mintel, Anonymous, "Auriga—Cernor Kit", Record ID 1630518, Sep. 2011, www.gnpd.com.
Mintel, Anonymous, "Drunk Elephant—Time To Wake Up A Morning Tonic for Skin", Record ID 7631131, May 2020, www.gnpd.com.
Mintel, Anonymous, "Drunk Elephant—Bare With Us The Love Kit", Record ID 7640457, May 2020, www.gnpd.com.
Mintel, Anonymous, "Drunk Elephant—Bare With Us The Love Kit", Record ID 77612403, May 2020, www.gnpd.com.
Mintel, Anonymous, "Drunk Elephant—Time To Wake Up A Morning Tonic for Skin", Record ID 7576779, Apr. 2020, www.gnpd.com.
Mintel, Anonymous, "Paula's Choice Boost—C15 Super Booster", Record ID 7201459, Jan. 2020, www.gnpd.com.
Mintel, Anonymous, "Pixi Skintreats Vitamin-C Chrsitmas 2019—Best of Vitamin-C Set", Record ID 7149163, Jan. 2020, www.gnpd.com.
Mintel, Anonymous, "Drunk Elephant—Rise + Glow Set", Record ID 7106385, Dec. 2019, www.gnpd.com.
Mintel, Anonymous, "Eighth Day—Dark Spot Rx", Record ID 6991279, Oct. 2019, www.gnpd.com.
Mintel, Anonymous, "Pixi Skintreats Vitamin C—Best of Vitamin C Set", Record ID 6529415 and 6449611, Apr. and May 2019, www.gnpd.com.
Mintel, Anonymous, "Eighth Day—Signature Collection", Record ID 6070639, Oct. 2018, www.gnpd.com.
Mintel, Anonymous, "Drunk Elephant—C-Firma Day Serum", Record ID 6038563, Oct. 2018, www.gnpd.com.
Mintel, Anonymous, "Eighth Day—Dark Spot Rx", Record ID 5955229, Oct. 2018, www.gnpd.com.
Mintel, Anonymous, "Korres—Rise & Shine Compete Shine Set", Record ID 5926015, Aug. 2018, www.gnpd.com.
Mintel, Anonymous, "Paula's Choice Boost—C15 Super Booster", Record ID 5821163 and 5821167, Jul. 2018, www.gnpd.com.
Mintel, Anonymous, "Paula's Choice Boost—C15 Super Booster", Record ID 5635233, Apr. 2018, www.gnpd.com.
Mintel, Anonymous, "Drunk Elephant—DayGLow Travel Sized Skin Care Set", Record ID 4533765, www.gnpd.com.
Mintel, Anonymous, "Skin Tone Correcting Daily Moisturiser UV SPF 30" Record ID 3060959, XP005874271, www.gnpd.com.
Mintel, Anonymous, "Clarifying Carection Cream" Record ID 3326113, XP005874273, www.gnpd.com.
Search Report issued to French counterpart Application No. 2103167 dated Dec. 20, 2021.
Mintel, anonymous, "Sun Perfector SPF 40+ PA++++", XP055856105, No. 7615847, May 12, 2020, www.gnpd.com.

(Continued)

*Primary Examiner* — Ganapathy Krishnan
(74) *Attorney, Agent, or Firm* — McNees Wallace & Nurick LLC

(57) ABSTRACT

An organic UVA filter-stabilized antioxidant system demonstrates stabilization after UV exposure as compared with controls lacking the UVA filter stabilizer. The organic UVA filter-stabilized antioxidant system provides a cosmetic composition that confers preserved and sustained antioxidant efficacy to keratinous tissue. The antioxidant system includes a combination of at least one hydroxycinnamate derivative, and an organic, water-soluble UVA filter in a water-based carrier.

20 Claims, No Drawings

(56) References Cited

OTHER PUBLICATIONS

Chaowattanapanit et al. "Postinflammatory hyperpigmentation: A comprehensive overview Treatment options and prevention" Journal of the American Academy of Dermatology, vol. 77, No. 4, 2017, pp. 607-621.
Manosroi et al. "Anti-aging efficacy of tropical formulations containing niosomes entrapped with rice bran bioactive compounds" Pharmaceutical Biology, vol. 50, No. 2, Feb. 1, 2012, pp. 208-224.
Ouimet et al. "Biodegradable Ferulic Acid-Containing Ply(anhydride-ester): Degradation Products with Controlled Release and Sustained Antioxidant Activity" Biomacromoledules, vol. 14, No. 3, Mar. 11, 2013, pp. 854-861.
Search Report issued to French counterpart Application No. 2100579 dated Oct. 29, 2021.

* cited by examiner

ORGANIC UVA FILTER-STABILIZED ANTIOXIDANT COMPOSITION

FIELD

This invention relates to a cosmetic composition for keratinous tissue, particularly skin, that includes an antioxidant component that is stabilized using a photoprotective organic UVA filter.

BACKGROUND

Environmental indoor and outdoor UV exposure and environmental pollution can accelerate skin aging by producing free radicals in skin. Antioxidants, including hydroxycinnamate derivates such as ferulic acid, Vitamin C, and other actives protect cells from the damage of oxidative stress by scavenging free radicals and inhibiting oxidation reactions. The topical application of antioxidants and other skin actives is broadly employed in skin care products to prevent skin aging and confer other protective benefits. Antioxidants are known to exhibit chemical properties that are associated with reduced tissue damage. Antioxidants are known to participate in sequestering chemically active species to prevent the formation of free radicals which can contribute to oxidative stress leading to aging of skin. But like the keratinous tissue that antioxidants are intended to protect, these chemical compounds are also prone to the damaging effects of UV radiation and can be rendered less efficacious or potent after UV exposure. Thus, there is a need for compositions that protect and/or stabilize antioxidants to preserve and sustain their efficacy in protecting keratinous tissue.

SUMMARY

The disclosure relates to an organic UVA filter-stabilized antioxidant system and a cosmetic composition comprising the antioxidant system that that demonstrates stabilization from decomposition of the at least one hydroxycinnamate derivative after UV exposure as compared with controls lacking the UVA filter stabilizer. The organic UVA filter-stabilized antioxidant system provides a cosmetic composition that confers preserved and sustained antioxidant efficacy to keratinous tissue. The antioxidant system includes a combination of at least one hydroxycinnamate derivative, ascorbic acid (Vitamin C) and an organic, water-soluble UVA filter in a water-based carrier. In an exemplary embodiment, the organic UVA filter-stabilized antioxidant system includes ferulic acid, ascorbic acid (Vitamin C) and terephthalylidene dicamphor sulfonic acid in a water-based carrier.

In some embodiments, the disclosure provides a cosmetic composition comprising:
(a) an organic UVA filter-stabilized antioxidant system comprising:
  i. at least one hydroxycinnamate derivative;
  ii. at least one organic water-soluble UVA filter; and
(b) a carrier system comprising a water phase.

In various embodiments, the cosmetic composition demonstrates stabilization of at least 50% and up to about 95% of a hydroxycinnamate derivative after classical urban daily exposure to UV radiation as compared with controls lacking the UVA filter stabilizer. In some embodiments, the cosmetic composition demonstrates stabilization after classical urban daily exposure to UV radiation as compared with controls lacking the UVA filter stabilizer from about 50% and up to about 55%. In some embodiments, stabilization is exhibited by preservation of at least 50% of the antioxidant active after classical urban daily exposure to UV radiation. In some particular embodiments, classical urban daily UV exposure is exposure of about 5 J/cm2, at a UVA flow of about 0.0037 W/cm2 for a period of time in a range from about 30 minutes to about 60 minutes.

In various embodiments, the cosmetic composition is formed by providing the carrier system having a water-phase that comprises water. In various embodiments, the carrier system may further comprise one more additional ingredients, each present in the water phase or in another phase, such as an oily phase. In various embodiments, the one or more additional ingredients includes one or more of a glycol, a humectant, a preservative, a surfactant, a thickener, an active compound, or a combination thereof. In some embodiments, the cosmetic composition may include one or more of any one of the additional ingredients. In some embodiments, the cosmetic composition may also include emulsifiers, emollients, fragrances, pH adjusters, other cosmetically acceptable additives, or a combination thereof.

In some particular embodiments, the cosmetic composition comprises one or a combination of additional ingredients selected from the group consisting of hexylene glycol, dipropylene glycol, laureth-23, sodium dilauramidoglutamide lysine (Pellicier) and sodium hydroxide.

The cosmetic composition may be any suitable form, such as, but not limited to, a single phase solution comprising the water phase, a multi-phase solution comprising at least one water phase, an emulsion comprising a water phase, such as, but not limited to, a water-in-oil emulsion, an oil-in-water emulsion, or a silicone-in-water emulsion. The cosmetic composition may be provided in a product form for application to keratinous tissue, such as, but not limited to, a skin care product or a hair care product, and may be a product form such as, but not limited to, a hydroglycolic solution, a micellar water, a cream or lotion, a toner, a cleanser, or a make-up remover. The cosmetic composition in any of the product forms may be either a leave-on or a rinse-off formulation.

In various embodiments, the at least one hydroxycinnamate derivative is present in the cosmetic composition in a range from about 0.1% to about 5%, by weight, based on the weight of the composition. In some particular embodiments, the at least one hydroxycinnamate derivative is ferulic acid.

In various embodiments, the composition may further include ascorbic acid is present in the cosmetic composition in a range from about 5% to about 30%, by weight, based on the weight of the composition, the ascorbic acid present in a ratio of water to ascorbic acid in a range from about 3:1 to about 10:1, based on the weight of the cosmetic composition.

In various embodiments, the at least one organic, water-soluble UVA filter is present in the cosmetic composition in a range from about 0.4% to about 10%, by weight, based on the weight of the composition. In some particular embodiments, the at least one organic, water-soluble UVA filter is terephthalylidene dicamphor sulfonic acid, (the product sold under the name Mexoryl™ SX).

In some embodiments, the cosmetic composition comprises one or a combination of phytic acid or chlorogenic acid, the phytic acid present in the cosmetic composition in a range from about 0.25% to about 10%, and the chlorogenic acid present in the cosmetic composition in a range from about 0.5% to about 1.5%, each by weight, based on the weight of the composition.

In some embodiments, the cosmetic composition comprises one or a combination of active compounds selected from the group consisting of Vitamin E (e.g. tocopherol), panthenol, hyaluronic acid, carnosine, at least one additional sun filter, at least one hydroxy acid, and combinations thereof. In some embodiments, an active compound is selected from the group consisting of alpha, beta or polyhydroxy acids selected from the group consisting of lactic acid, glycolic acid, salicylic acid, malic acid, tartaric acid, citric acid, mandelic acid, lactobionic acid, gluconolactone, galactose, and combinations thereof.

In some embodiments, the cosmetic composition comprises one or a combination of active compounds selected from the group consisting of tocopherol, panthenol and hyaluronic acid.

In some embodiments, the disclosure provides a cosmetic composition comprising phytic acid, chlorogenic acid, or a combination thereof in the antioxidant system. In some embodiments, the cosmetic composition comprises both phytic acid and chlorogenic acid in the antioxidant system.

In some embodiments, the disclosure provides a cosmetic composition comprising:
(a) an organic UVA filter-stabilized antioxidant system comprising:
  i. at least one hydroxycinnamate derivative;
  ii. ascorbic acid;
  iii. at least one organic water-soluble UVA filter; and
(b) a carrier system comprising: a water phase, and one or more additional components comprising a glycol, a humectant, a preservative, a surfactant, a thickener, an active compound, an emulsifier, an emollient, or a combination thereof.

In some particular embodiments, the at least one hydroxycinnamate derivative is present in a range from about 0.2% to about 5%, the ascorbic acid is present in a range from about 5% to about 30%, the at least one organic water-soluble UVA filter is present in a range from about 0.4% to about 10%, and, optionally: phytic acid is present in a range from about 0.25% to about 10% or chlorogenic acid is present in a range from about 0.25% to about 10%, or a combination thereof, all amounts by weight, based on the weight of the composition.

In some particular embodiments, the carrier system comprises one or a combination of additional ingredients selected from the group consisting of hexylene glycol, dipropylene glycol, laureth-23, sodium dilauramidoglutamide lysine (Pellicier) and sodium hydroxide, and one or a combination of active compounds selected from the group consisting of tocopherol, panthenol and hyaluronic acid.

In some embodiments, the disclosure provides a cosmetic composition comprising:
(a) an organic UVA filter-stabilized antioxidant system comprising:
  i. at least one hydroxycinnamate derivative comprising ferulic acid present in a range from about 0.2% to about 5%;
  ii. ascorbic acid present in a range from about 5% to about 30%;
  iii. at least one organic water-soluble UVA filter comprising terephthalylidene dicamphor sulfonic acid present in a range from about 0.4% to about 10%;
  iv. phytic acid present in a range from about 0.25% to about 10% and chlorogenic acid present in a range from about 0.25% to about 10%, or a combination thereof;
  all amounts by weight, based on the weight of the composition; and
(b) a carrier system comprising a water phase and one or a combination of additional ingredients selected from the group consisting of hexylene glycol, dipropylene glycol, laureth-23, sodium dilauramidoglutamide lysine (Pellicier) and sodium hydroxide, and one or a combination of active compounds selected from the group consisting of tocopherol, panthenol and hyaluronic acid.

These and other aspects of the invention are set out in the appended claims and described in greater detail in the detailed description of the invention.

This disclosure describes exemplary embodiments in accordance with the general inventive concepts and is not intended to limit the scope of the invention in any way. Indeed, the invention as described in the specification is broader than and unlimited by the exemplary embodiments set forth herein, and the terms used herein have their full ordinary meaning.

It is to be understood that both the foregoing general description and the following detailed description are exemplary and explanatory only and are not restrictive of the disclosure.

DETAILED DESCRIPTION

"Cosmetically acceptable" means a carrier that is compatible with any keratinous substrate.

"Keratinous substrate" and "keratinous tissue" each includes but is not limited to skin, hair, and nails.

The disclosure relates to an organic UVA filter-stabilized antioxidant system and a cosmetic composition comprising the antioxidant system that that demonstrates stabilization from decomposition of the at least one hydroxycinnamate derivative after UV exposure as compared with controls lacking the UVA filter stabilizer. The organic UVA filter-stabilized antioxidant system provides a cosmetic composition that confers preserved and sustained antioxidant efficacy to keratinous tissue. The antioxidant system includes a combination of at least one hydroxycinnamate derivative, ascorbic acid (Vitamin C) and an organic, water-soluble UVA filter in a water-based carrier. In an exemplary embodiment, the organic UVA filter-stabilized antioxidant system includes ferulic acid, ascorbic acid (Vitamin C) and terephthalylidene dicamphor sulfonic acid in a water-based carrier.

In some embodiments, the water-based carrier is a water phase that may further include one or more other ingredients for providing one of a variety of forms of cosmetic products, the ingredients including but not limited to a glycol, a humectant, a preservative, a surfactant, a thickener, an active compound, or a combination thereof.

The cosmetic composition may also include emulsifiers, emollients, fragrances, pH adjusters, other cosmetically acceptable additives, or a combination thereof. For the avoidance of doubt, the cosmetic composition may include one or more of any one of the additional ingredients. For example, the cosmetic composition may include one, or more than one glycol, or one, or more than one humectant, and the like. It will be understood that additional ingredients, when present, are present in the carrier system in either a water phase or an oily phase.

The cosmetic composition may be any suitable cosmetic composition, such as, but not limited to, a single phase solution comprising the water phase, a multi-phase solution comprising at least one water phase, an emulsion comprising a water phase, such as, but not limited to, a water-in-oil emulsion, an oil-in-water emulsion, or a silicone-in-water emulsion. The cosmetic composition may be provided in a product form for application to keratinous tissue, such as, but not limited to, a skin care product or a hair care product, and may be a product form such as, but not limited to, a hydroglycolic solution, a micellar water, a cream or lotion, a toner, a cleanser, or a make-up remover. The cosmetic composition in any of the product forms may be either a leave-on or a rinse-off formulation.

In some embodiments, the cosmetic composition according to the disclosure is a single phase solution that comprises one or more solutes dissolved in one or more solvents to form a substantially homogeneous liquid that appears to be substantially clear to the naked eye. In one such embodiment, the cosmetic composition is a single phase water solution. In some particular embodiments, the cosmetic composition is a hydroglycolic solution that comprises one or a combination of glycols.

The inventors have shown the surprising and unexpected effect of the combination of at least one hydroxycinnamate derivative, ascorbic acid (Vitamin C) and an organic, water-soluble UVA filter as a stabilizer of antioxidant stability and activity after clinically significant UV exposure. Using this combination, the cosmetic composition demonstrates stabilization of at least 50% and up to about 95% of a hydroxycinnamate derivative after classical urban daily exposure to UV radiation as compared with controls lacking the UVA filter stabilizer. In some embodiments, the cosmetic composition demonstrates stabilization after classical urban daily exposure to UV radiation as compared with controls lacking the UVA filter stabilizer from about 50% and up to about 55%. In some embodiments, stabilization is exhibited by preservation of at least 50% of the antioxidant active after classical urban daily exposure to UV radiation. In some particular embodiments, UV exposure means exposure of about 5 J/cm$^2$, at a UVA flow of about 0.0037 W/cm$^2$ for a period of time in a range from about 30 minutes to about 60 minutes.

It will be appreciated then that the stabilization of the hydroxycinnamate derivative, for example, ferulic acid, may be in the range from about at least 50, 55, 60, 65, 70, 75, 80, 85, 90, to about 95 percent and in some particular embodiments may be in the range from about at least 50, 51, 52, 53, 54, to about 55 percent, including increments and ranges there between.

It will be appreciated that classical urban daily exposure to UV radiation is exposure within a range from about 2 J/cm$^2$ to 20 J/cm$^2$ at a UVA flow of from about 0.0020 W/cm$^2$ to 0.0080 W/cm$^2$ for a period of time in a range from about 30 minutes to about 60 minutes, or from about 10 to about 30 minutes, or from about 10 to about 360 minutes, and in some particular embodiments classical urban daily exposure, based on indoor exposure is about 5 J/cm$^2$, at a UVA flow of about 0.0037 W/cm$^2$ for a period of time in a range from about 30 minutes to about 60 minutes. It will be understood that more generally the total UV dallying dose in NY, NY in the month of April averages about 38 J/cm$^2$.

Organic UVA Filter-Stabilized Antioxidant System

In accordance with the disclosure, embodiments of the cosmetic composition include an organic UVA filter-stabilized antioxidant system comprising a combination of a combination of at least one hydroxycinnamate derivative, ascorbic acid (Vitamin C) and an organic, water-soluble UVA filter in a water-based carrier. In some particular embodiments, the cosmetic composition comprises each of includes ferulic acid, ascorbic acid (Vitamin C) and terephthalylidene dicamphor sulfonic acid in a water-based carrier.

Hydroxycinnamate Derivative

In the various embodiments, the cosmetic composition comprises a hydroxycinnamate derivative, for example, ferulic acid. A cinnamic acid or derivative thereof includes ferulic acid, p-coumaric acid, caffeic acid, sinapinic acid, chlorogenic acids, caftaric acid, chicoric acid, coutaric acid, rosmarinic acid, derivatives thereof, and combinations thereof. Equivalent derivatives thereof include those cinnamic acid derivatives having substitutions on the hydroxyl groups of the aromatic ring such as short chain aliphatic groups (one to six carbon atoms) or long chain aliphatic groups (seven to twenty-four carbon atoms) to form an ether, or such aliphatic groups substituted with alkyl, alkoxy, hydroxyl, amino, or amido, for example, to form a substituted ether. Equivalent derivatives thereof further include those cinnamic acid derivatives having modifications of the methoxy group(s) of the aromatic ring to short chain aliphatic groups (two to six carbon atoms) or to long chain aliphatic groups (seven to twenty-four carbon atoms) to form a longer chain ether, or such aliphatic groups substituted with alkyl, alkoxy, hydroxyl, amino, or amido, for example, to form a substituted long chain ether. The 3-carboxy group of a cinnamic acid derivative may also be converted to esters or amides having aliphatic groups of up to 24 carbons or an aromatic group, for example. Cis and trans isomers of the cinnamic acid derivatives are included herein since the cis isomer is readily converted to the trans isomer. Salts of the cinnamic acid derivatives are included herein. In one embodiment, the cinnamic acid derivative is a triethanolamine salt. Caffeic acid, also known as 3-(3,4-dihydroxyphenyl)-2-propenoic acid, is found in many fruits, vegetables, seasonings and beverages consumed by humans. Caffeic acid is present in such goods in conjugated forms such as chlorogenic acid. Para-coumaric acid, also known as 3-(4-hydroxyphenyl)-2-propenoic acid or p-hydroxycinnamic acid, is found in various plants, including lignin forming plants. Trans-ferulic acid, also known as 3-(4-hydroxy-3-methoxyp-henyl)-2-propenoic acid or 4-hydroxy-3-methoxycinnamic acid, is also widely distributed in small amounts in plants. Sinapinic acid, also known as 3,5-dimethoxy4-hydroxycinnamic acid, is from black mustard seeds. Caffeic acid, para-coumaric acid, trans-ferulic acid and sinapinic acid are commercially available from Sigma-Aldrich.

Cinnamic acid derivatives, including, but not limited to ferulic acid, and triethanolamine salts may be present in the cosmetic composition in an amount from about 0.1% to about 5%, and in some embodiments, from about 0.1% to about 3%, and in some embodiments, from about 0.5% to about 1.0%, or any suitable combination, sub-combination, range, or sub-range thereof by weight, based on the weight of the cosmetic composition.

Ascorbic Acid

In the various embodiments, the cosmetic composition comprises ascorbic acid, or Vitamin C.

In some embodiments, pH of the cosmetic composition is in a range that includes about 3.5 to about 7.0, and is in some embodiments, greater than 4.0. In some embodiments that include ascorbic acid, a pH close to 3.5 or 4.0 ensures that greater than about 82% of the ascorbic acid remains in a protonated, uncharged form as disclosed in U.S. Pat. No. 5,140,043, Aug. 18, 1992, the entire disclosure of which is incorporated by reference herein. Ascorbic acid may be provided by the addition of any reducing analog of ascorbic acid, such as D-isoascorbic acid or by the addition of other small reducing compounds such as, but not limited to, glutathione, L-cysteamine, and the like. Such forms would be expected to provide an equivalent composition to that claimed and are within the scope of the invention.

Ascorbic acid and its derivatives may be present in the cosmetic composition in an amount from about 1% to about 30%, and in some embodiments, from about 5% to about 25%, and in some embodiments, from about 10% to about 20%, and in some embodiments, from about 10% to about 15%, or any suitable combination, sub-combination, range, or sub-range thereof by weight, based on the weight of the cosmetic composition.

Phytic and Chlorogenic Acids

In various embodiments, the cosmetic composition may comprise at least one or a combination of phytic acid and chlorogenic acid. In some particular embodiments, the cosmetic composition comprises phytic acid. Phytic acid is also known as phytate and is a six-fold dihydrogenphosphate ester of inositol (specifically, of the myo isomer), also called inositol hexakisphosphate (IP6) or inositol polyphosphate. At physiological pH, the phosphates are partially ionized, resulting in the phytate anion. Phytic acid is found naturally in plant seeds and is a storage form of phosphorus. In some other embodiments, the cosmetic composition comprise chlorogenic acid. Chlorogenic acid is also known as chlorogenate or 3-caffeoylquinate and belongs to the class of organic compounds known as quinic acids and derivatives. Chlorogenic acid is the ester of caffeic acid (a hydroxycinnamic acid related to ferulic acid, as described herein above) and (−)-quinic acid.

Phytic acid may be present in the cosmetic composition in an amount from about 0.5% to about 5%, and in some embodiments, from about 1% to about 4%, and in some embodiments, from about 1% to about 2%, or any suitable combination, sub-combination, range, or sub-range thereof by weight, based on the weight of the cosmetic composition. As exemplified in the instant disclosure, the phytic acid raw material is provided at a dilution of 50% such that the exemplified percent, by weight, based on the weight of the cosmetic compositions, in the cosmetic composition are multiplied by 0.5 to obtain the final percent, by weight, based on the weight of the cosmetic composition, of phytic acid.

Chlorogenic acid may be present in the cosmetic composition in an amount from about 0.5% to about 1.5%, and in some embodiments, from about 1% to about 1.5%, and in some embodiments, from about 1.1% to about 1.2%, or any suitable combination, sub-combination, range, or sub-range thereof by weight, based on the weight of the cosmetic composition.

Thus, in various embodiments, each of the components of hydroxycinnamate derivatives, ascorbic acid, and phytic and chlorogenic acid when present, are present in a cosmetic composition according to the disclosure, and each of the individual components in the ranges as described herein above, from about 0.01, 0.02, 0.03, 0.04, 0.05, 0.06, 0.07, 0.08, 0.09, 0.10, 0.20, 0.30, 0.40, 0.50, 0.60, 0.70, 0.80, 0.90, 1.0, 2, 3, 4, 5, 6, 7, 8, 9, 10, 11, 12, 13, 14, 15, 16, 17, 18, 19, 20, 21, 22, 23, 24, 25, 26, 27, 28 to about 30 percent by weight, including increments and ranges there between.

UVA Filter Stabilizer

In the various embodiments, the cosmetic composition comprises at least one UVA filter stabilizer. The UVA filter stabilizer is a water soluble organic UVA filter. In various embodiments, the sunscreen composition comprises one or a combination of organic UV filters. The organic UV filters is active in the UV-A region. In some embodiments, the organic UV filter is selected from camphor compounds, in particular, benzylidenecamphor derivatives: 3-benzylidene camphor, manufactured under the trademark MEXORYL™ as "Mexoryl SD" by Chimex; 4-methylbenzylidene camphor, marketed under the trademark "Eusolex 6300" by Merck; benzylidene camphor sulfonic acid, "Mexoryl SL" by Chimex; camphor benzalkonium methosulfate, "Mexoryl SO" by Chimex; terephthalylidene dicamphor sulfonic acid, "Mexoryl SX" by Chimex; and polyacrylamidomethyl benzylidene camphor, "Mexoryl SW" by Chimex.

Each of the at least one UVA filter stabilizer is present in the cosmetic composition in an amount from about 0.4% to about 10%, and in some embodiments, from about 1% to about 8%, and in some embodiments, from about 3% to about 5%, or any suitable combination, sub-combination, range, or sub-range thereof by weight, based on the weight of the cosmetic composition.

Thus, a UVA filter stabilizer is present in the cosmetic composition, by weight, based on the total weight of the composition, from about 0.04, 0.05, 0.06, 0.07, 0.08, 0.09, 0.10, 0.20, 0.30, 0.40, 0.50, 0.60, 0.70, 0.80, 0.90, 1.0, 2, 3, 4, 5, 6, 7, 8, 9, to about 10 percent, by weight, based on the weight of the cosmetic composition, including increments and ranges therein and there between.

Carrier System

In various embodiments, the cosmetic composition is formed by providing a carrier system having a water-phase that comprises water.

Water

In accordance with the various embodiments, water is present in the cosmetic composition in a range from about 10% to about 95%, and in some embodiments, from about 25% to about 80%, and in some embodiments, from about 30% to about 65%, and in some embodiments, from about 35% to about 50%, or any suitable combination, sub-combination, range, or sub-range thereof by weight, based on the weight of the cosmetic composition. One of ordinary skill in the art, however, will appreciate that other ranges are within the scope of the invention. Thus, water is present, by weight, based on the total weight of the cosmetic composition, from about 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, to about 75 percent, by weight, including increments and ranges therein and there between. One of ordinary skill in the art, however, will appreciate that other ranges are within the scope of the invention.

The water used may be chosen from, for example, sterile demineralized water and/or a floral water such as rose water, cornflower water, chamomile water or lime water, and/or a natural thermal or mineral water such as, for example: water from Vittel, water from the Vichy basin, water from Uriage, water from La Roche Posay, water from La Bourboule, water from Enghien-les-Bains, water from Saint Gervais-les-Bains, water from Neris-les-Bains, water from Allevar-les-Bains, water from Digne, water from Maizieres, water from Neyrac-les-Bains, water from Lons-le-Saunier, water from Eaux Bonnes, water from Rochefort, water from Saint Christau, water from Les Fumades, water from Tercis-les-Bains or water from Avene. The water phase may also comprise reconstituted thermal water, that is to say a water comprising trace elements such as zinc, copper, magnesium, etc., reconstituting the characteristics of a thermal water.

The pH of the cosmetic composition is not limited but is generally between 3.0 and 4.0, and in some embodiments, is one of between 3 and 3.5. The pH can be adjusted to the desired value by addition of a base (organic or inorganic) to the cosmetic composition, for example ammonia or a primary, secondary or tertiary (poly)amine, such as monoethanolamine, diethanolamine, triethanolamine, isopropanolamine or 1,3-propanediamine, or alternatively by addition of an inorganic or organic acid, advantageously a carboxylic acid, such as, for example, citric acid. It will be understood by a skilled artisan that pH is a measurement of the hydrogen ion concentration in water which is determined by measuring the electrode potential using electrodes attached to a pH meter. It will be further understood that, due to the intrinsic variability in pH measurements, a skilled artisan would expect at least a 10% variability in pH measurements of compositions such as disclosed herein when measured in a typical laboratory by a typical skilled person using a typical pH meter.

Other Ingredients

In various embodiments, the cosmetic composition also comprises one more additional ingredients, such as, but not limited to, a glycol, a humectant, a preservative, a surfactant, a thickener, an active compound, or a combination thereof. For the avoidance of doubt, the cosmetic composition may include one or more of any one of the additional ingredients. For example, the cosmetic composition may include one, or more than one glycol, or one, or more than one humectant, and the like. It will be understood that additional ingredients, when present, are present in the carrier system in either a water phase or an oily phase.

The cosmetic composition may be any suitable cosmetic composition, such as, but not limited to, a single phase solution comprising the water phase, a multi-phase solution comprising at least one water phase, an emulsion comprising a water phase, such as, but not limited to, a water-in-oil emulsion, an oil-in-water emulsion, or a silicone-in-water emulsion. The cosmetic composition may be provided in a product form for application to keratinous tissue, such as, but not limited to, a skin care product or a hair care product, and may be a product form such as, but not limited to, a hydroglycolic solution, a micellar water, a leave-on cream or lotion, a toner, a cleanser, or a make-up remover.

In some embodiments, the cosmetic composition comprises one or a combination of active compounds selected from the group consisting of Vitamin E, carnosine, hyaluronic acid, panthenol, at least one sun filter, at least one hydroxy acid, and combinations thereof. In some embodiments, an active compound is selected from the group consisting of alpha, beta or polyhydroxy acids selected from the group consisting of lactic acid, glycolic acid, salicylic acid, malic acid, tartaric acid, citric acid, mandelic acid, lactobionic acid, gluconolactone, galactose, and combinations thereof.

In various embodiments, the cosmetic composition further includes one or more additives selected from emulsifiers, emollients, fragrances, pH adjusters, other cosmetically acceptable additives, or a combination thereof, and is free or essentially free of powders and solid particles, including but not limited to, titanium dioxide, zinc oxide, tin oxide, iron oxides, mica, silica, ferric ferrocyanide, alumina, silicates, synthetic fluorphlogopite, polyethylene, polypropylene, poly methyl methacrylate, talc, perlites, hectorites, bentonite, kaolin, pumice, boron nitride, and combinations thereof. In some particular embodiments, the cosmetic composition excludes propylene glycol or butylene glycol.

Humectants/Glycols

In accordance with the disclosure, one or more humectants may be present in the cosmetic composition.

In some embodiments, the humectant may comprise one or more of polyols, including, for example, hexylene glycol, dipropylene glycol, glycerin, glycerol, glycols, such as, caprylyl glycol, butylene glycol, propylene glycol, isoprene glycol, polyethylene glycol, monoethylene glycol, diethylene glycol, triethylene glycol, diethylene glycol, hexylene glycol, glycol ethers, such as, monopropylene, dipropylene and tripropylene glycol alkyl(C1-C4)ethers, squalane, triacetin, sugars, such as, glucose, xylitol, maltitol, sorbitol, sucrose pentaerythritol, inositol, pyrrolidone carboxylic acid, lactic acid, lithium chloride, acetamide MEA, sodium lactate, urea, dicyanamide, hyaluronic acid, aloe vera, honey, and seaweed extract.

In accordance with some embodiments, glycols, when present, may be present in the cosmetic composition alone or with at least one other glycol, each glycol present in an amount that is in a range from about 0.1% to about 30%, or from about 5% to about 25%, or from about 10% to about 15%, or any suitable combination, sub-combination, range, or sub-range thereof by weight, based on the weight of the composition, by weight, based on the weight of the cosmetic composition. In some embodiments, the total amount of glycol is less than about 30%, for example, the total is about 29.5%, or about 29%. As provided herein, some glycols, when present alone in the cosmetic composition, are present in an amount that is at least about 8%, or at least about 8.5%, or at least about 9%, or at least about 9.5%, or at least about 10%, or at least about 10.5%.

Thus, in various embodiments, each of the glycols is present in a cosmetic composition according to the disclosure, each alone and/or in combinations as described in the paragraphs set forth herein above from about 0.1, 0.2, 0.3, 0.4, 0.5, 0.6, 0.7, 0.8, 0.9, 1.0, 1.5, 2, 3, 4, 5, 6, 7, 8, 9, 10, 11, 12, 13, 14, 15, 16, 17, 18, 19, 20, 21, 22, 23, 24, 25, 26, 27, 28, 29 to less than about 30 percent, by weight, including increments and ranges therein and there between.

In some embodiments, the composition includes a glycol humectant comprising one or a combination of hexylene glycol and dipropylene glycol.

In accordance with the various embodiments, the amount of humectant present in the cosmetic composition can range from about 1% to about 10%, or from about 1% to about 8%, or from about 1% to about 5%, or from about 2% to about 3%, or any suitable combination, sub-combination, range, or sub-range thereof by weight, based on the weight of the composition. One of ordinary skill in the art, however, will appreciate that other ranges are within the scope of the invention.

Thus, any one of or a combination of humectant, when present, may be present, by weight, based on the total weight of the composition, is from about 1, 2, 3, 4, 5, 6, 7, 8, 9, to about 10 percent, by weight, based on the weight of the cosmetic composition, including increments and ranges therein and there between.

Surfactant

In accordance with the disclosure, various non-limiting embodiments of the cosmetic composition may optionally include at least one surfactant. And in accordance with the disclosure, various non-limiting embodiments of the cosmetic composition that include an oil, for example, but not limited to, a Vitamin E component, such as tocopherol, may optionally include at least one surfactant. In some embodiments, the cosmetic composition comprises no oil. In some embodiments, the cosmetic composition comprises no surfactant. In some embodiments, the cosmetic composition comprises at least one oil, for example, tocopherol, with at least one surfactant. In some embodiments, the cosmetic composition comprises at least one oil with more than one surfactant. In some embodiments, the cosmetic composition comprises at least one oil without any surfactants, wherein the total amount of oil present does not inhibit forming the cosmetic composition as a clear, single phase solution.

The at least one surfactant may be a nonionic, cationic, anionic, or a zwitterionic surfactant. The at least one surfactant may be selected from the group consisting of laureth-23, sodium dilauramidoglutamide lysine, polyoxyethylene sorbitan monolaureate, polyoxyethylated octyl phenol, 3-((3-cholamidopropyl) dimethylammonio)-1 propane sulfonate, cholate, deoxycholate, sodium dodecylsulfate, TWEEN-80, and combinations thereof. The at least one surfactant may exclude esters. The at least one surfactant may be present in the cosmetic composition in a range from about 1% to about 5%, based on the weight of the cosmetic composition.

In some particular embodiments the at least one surfactant, when present, comprises one or a combination of laureth-23 and sodium dilauramidoglutamide lysine. In some particular embodiments the cosmetic composition comprises two or more surfactants, for example, a combination of laureth-23 and sodium dilauramidoglutamide lysine.

In various embodiments, the at least one surfactant, when present, may be present from about 0.1% to about 10%, or from about 1% to about 5% by weight of the cosmetic composition, and in some embodiments, from about 1% to about 2%, and in some embodiments, from about 3% to about 6%, and in some embodiments, from about 3% to about 4.5%, or any suitable combination, sub-combination, range, or sub-range thereof by weight, based on the weight of the cosmetic composition. In some embodiments, laureth-23 may be present from about 1% to about 5% by weight of the cosmetic composition, and in some embodiments, from about 3% to about 4.5%, or any suitable combination, sub-combination, range, or sub-range thereof by weight, based on the weight of the cosmetic composition. In some embodiments, polyoxyethylene sorbitan monolaureate may be present from about 1% to about 5% by weight of the cosmetic composition, and in some embodiments, from about 1% to about 2%, or any suitable combination, sub-combination, range, or sub-range thereof by weight, based on the weight of the cosmetic composition. In some embodiments, the cosmetic composition comprises more than one surfactant. One of ordinary skill in the art, however, will appreciate that other ranges are within the scope of the invention.

Thus, in various embodiments, when present, each of the at least one surfactant may be present in a cosmetic composition according to the disclosure from about 1, 2, 3, 4, to about 5 percent, by weight, including increments and ranges therein and there between.

Preservatives

In accordance with the disclosure, one or more preservatives and/or antimicrobials may be present in the cosmetic composition. Any preservative commonly used in cosmetic formulations is an acceptable preservative for the cosmetic composition herein, such as phenoxyethanol, members from the paraben family such as the methyl, ethyl, propyl, butyl or isobutyl parabens, 4-hydroxy benzoic acid, benzoic acid, sorbic acid, dehydroacetic acid, triclosan, benzyl alcohol, chlorophenesin, or salicylic acid, for example. At more concentrated amounts of suitable solvents for optional additives, in particular, suitable solvents for antimicrobials and preservatives, members from the paraben family may be used as a preservative.

In some embodiments, the preservative may comprise one or more preservatives selected from the group consisting of organic acids, parabens, formaldehyde donors, phenol derivatives, quaternary ammoniums, alcohols, isothiazolinones, and combinations thereof. Preservatives having antibacterial activity are optionally present in the cosmetic composition of the present invention. Examples of organic acid preservatives include, but are not limited to, sodium benzoate, potassium sorbate, benzoic acid and dehydroacetic acid, sorbic acid, and combinations thereof. A preferred organic acid preservative system includes a mixture of sodium benzoate and potassium sorbate. Examples of paraben preservatives include, but are not limited to, alkyl para-hydroxybenzoates, wherein the alkyl radical has from 1, 2, 3, 4, 5 or 6 carbon atoms and for example, from 1 to 4 carbon atoms e.g., methyl para-hydroxybenzoate (methylparaben), ethyl para-hydroxybenzoate (ethylparaben), propyl para-hydroxybenzoate (propylparaben), butyl para-hydroxybenzoate (butylparaben) and isobutyl para-hydroxybenzoate (isobutylparaben). Examples of formaldehyde donor preservatives include, but are not limited to, 1,3-Dimethylol-5,5-dimethylhydantoin (DMDM hydantoin), imidazolidinyl urea, gluteraldehyde, and combinations thereof. Examples of quaternary ammonium preservatives include, but are not limited to, benzalkonium chloride, methene ammonium chloride, benzethonium chloride, and combinations thereof. Examples of alcohol preservatives include, but are not limited to, ethanol, benzyl alcohol, dichlorobenzyl alcohol, phenoxyethanol, and combinations thereof. Examples of isothiazolone preservatives include, but are not limited to, methylchloroisothiazolinone, methylisothiazolinone, and combinations thereof.

Other suitable preservatives include, but are not limited to, phenoxyethanol, chloroacetamide, triclosan and iodopropynyl butylcarbamate, pyridine derivatives (e.g., pyrithione and zinc pyrithione), chlorphenesin, phenyl mercuric salts, and other known preservative systems.

In some particular embodiments the at least one preservatives, when present, comprises phenoxyethanol.

In some embodiments, the preservative may include one or more preservatives, the one or combination present at a concentration, by weight of about 0.001% to about 5%, or alternatively about 0.05% to about 2.5% or alternatively about 0.1% to about 2.0%, based upon weight of the composition.

Thus, any one of or a combination of preservatives, when present, may be present, by weight, based on the total weight of the composition, is from about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 1.0, 1.1, 1.2, 1.3, 1.4, 1.5, 1.6, 1.7, 1.8, 1.9, 2, 3, 4, to about 5 percent, by weight, based on the weight of the cosmetic composition, including increments and ranges therein and there between.

Polymeric Thickener

In accordance with the various embodiments, the composition may include one or more polymeric thickeners. In some embodiments, the one or more thickener may be selected from one or more of natural gums and synthetic polymers, for example, the thickener may be selected from the group consisting of starches (corn, rice, tapioca, potato), gums (xanthan carrageenan, gellan, sclerotium, tarabiotech fermentation). In some particular embodiments, the thickener may be selected from acrylates/C10-30 alkyl acrylate crosspolymer, carbomer, xanthan gum, hydroxypropyl guar, ceratonia siliqua (carob) gum, ammonium polyacryloyldimethyl taurate, ammonium acryloyldimethyltaurate/steareth-25 methacrylate crosspolymer, and polyacrylate crosspolymer-6.

In some embodiments, the polymeric thickener may be one of carbomer, acrylates/C10-30 alkyl acrylate crosspolymer, polyacrylate crosspolymer-6, microcrystalline cellulose (and) cellulose gum, xanthan gum, sodium carboxymethyl starch, sclerotium gum (and) xanthan gum, xanthan gum (and) ceratonia siliqua (carob) gum (50/50), dehydroxanthan gum, hydroxypropyl starch phosphate, sclerotium gum (and) xanthan gum (75/25), sclerotium gum, xanthan gum (and) sclerotium gum (and) Lecithin (and) pullulan, or combinations thereof.

In some embodiments the composition may comprise two or more polymeric thickeners. The amount of each of the at least one polymeric thickener, when present, may be present in the cosmetic composition in a range of from about 0.01% to about 2%, or from about 0.01% to about 1.5%, or from about 0.3% to about 1.2%, or any suitable combination, sub-combination, range, or sub-range thereof by weight, based on the weight of the composition. One of ordinary skill in the art, however, will appreciate that other ranges are within the scope of the invention.

In some embodiments, the total amount of polymeric thickener in the cosmetic composition, when present, is present from about 0.01% to about 5%, or from about 0.02% to about 2%, or from about 0.03% to about 1.5%, or from about 0.1% to about 0.2%, or any suitable combination, sub-combination, range, or sub-range thereof by weight, based on the weight of the composition. One of ordinary skill in the art, however, will appreciate that other ranges are within the scope of the invention.

Thus, one or more polymeric thickener, when present, is present by weight, based on the total weight of the composition, from about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.5, 4.0, 4.5 to about 5.0 percent, including increments and ranges therein and there between.

Optional Active Compounds

In accordance with the disclosure, embodiments of the cosmetic composition may include one or more additional compounds selected from active compounds, in particular keratinous tissue actives, such as, but not limited to, skin actives. In some embodiments, optional active compounds may be selected from the group consisting of: vitamins, for example, Vitamin E, carnosine, hyaluronic acid, panthenol, at least one sun filter, at least one hydroxy acid, and combinations thereof. In some embodiments, an active compound is selected from the group consisting of alpha, beta or polyhydroxy acids selected from the group consisting of lactic acid, glycolic acid, salicylic acid, malic acid, tartaric acid, citric acid, mandelic acid, lactobionic acid, gluconolactone, galactose, and combinations thereof. For the avoidance of doubt, the cosmetic composition may include one or more of any one of the optional active compounds. For example, the cosmetic composition may include one, or more than one hydroxy acid, one, or more than one vitamin, and the like.

Vitamin E may be selected from the group consisting of alpha-tocopherol, beta-tocopherol, delta-tocopherol, gamma-tocopherol, and alpha-tocotrienol, beta-tocotrienol, delta-tocotrienol, gamma-tocotrienol, and derivatives thereof. Salts or derivatives of tocopherols include pharmaceutically acceptable compounds such as acetate, sulfate, succinate, nicotinate, palmitate, allophanate, phosphate, quinone, or halogenated derivatives, esters, or stereoisomers, for example. The invention encompasses the use of Vitamin E derivatives in which substitutions, additions, and other alterations have been made in the 6-chromanol ring and/or side chain, with the proviso that the derivatives maintain the antioxidant activity of Vitamin E. Additional tocopherols can be constructed by conjugation to the ring structure or side chain of various other moieties, such as those containing oxygen, nitrogen, sulfur and/or phosphorus. Tocopherol derivatives can also be made by modifying the length of the side chain from that found in tocopherols such as alpha-, beta-, delta- and gamma-tocopherol. Tocopherols can also vary in stereochemistry and saturation of bonds in the ring structure and side chain. Additional tocopherol derivatives, including prodrugs, can be made by conjugation of sugars or other moieties to the side chain or ring structure. Tocopherols include without limitation stereoisomers (e.g., + and − stereoisomers of alpha-tocopherol; (+/−) indicates a racemic mixture) or mixtures of structurally distinct tocopherols (e.g., alpha-plus gamma-tocopherol). Tocopherols may be obtained from Roche, Nutley, N.J., for example.

In some embodiments, additional actives can also include at least one hydroxy acid selected from alpha, beta or polyhydroxy acids. Thus, in various embodiments, a hydroxy acid may be selected from the group consisting of lactic acid, glycolic acid, salicylic acid, malic acid, tartaric acid, citric acid, mandelic acid, lactobionic acid, gluconolactone, galactose, and combinations thereof.

In some embodiments, additional actives can also include one or more of the antioxidants selected from the group consisting of mangiferin, baicalin, resveratrol, tannic acid, polyphenols, amino acids and derivatives thereof, imidazoles, carnosine derivatives, carotenoids, carotenes (such as α-carotene, β-carotene, and lycopene), vitamin A, co-enzyme Q10, bioflavonoids, glutathione, plant extracts (such as rosemary extract, olive leaf extracts), green tea extracts, and combinations thereof.

In some particular embodiments, the cosmetic composition includes a combination of active compounds present in the cosmetic composition comprising a hydroxy acid, tocopherol, panthenol, hyaluronic acid, or a combination thereof.

Generally, each of the optional active compounds is present in the cosmetic composition in an amount from about 0.1% to about 30%, and in some embodiments, from about 0.5% to about 30%, and in some embodiments, from about 0.5% to about 15%, and in some embodiments, from about 0.1% to about 1%, and in some embodiments, from about 1% to about 2%, or any suitable combination, sub-combination, range, or sub-range thereof by weight, based on the weight of the cosmetic composition.

Vitamin E and its derivatives, including, but not limited to tocopherol, may be present in the cosmetic composition in an amount from about 0.5% to about 2%, and in some embodiments, from about 0.5% to about 1%, and in some embodiments, from about 1% to about 2.0%, or any suitable combination, sub-combination, range, or sub-range thereof by weight, based on the weight of the cosmetic composition.

One or more of hyaluronic acid, panthenol, and carnosine may be present in the cosmetic composition in an amount from about 0.1% to about 5%, and in some embodiments, from about 0.1% to about 3%, and in some embodiments, from about 0.5% to about 1.0%, or any suitable combination, sub-combination, range, or sub-range thereof by weight, based on the weight of the cosmetic composition.

Hyaluronic acid may be present in the cosmetic composition in an amount from about 0.01% to about 1%, and in some embodiments, from about 0.01% to about 0.1%, and in some embodiments, from about 0.05% to about 0.07%, or any suitable combination, sub-combination, range, or sub-range thereof by weight, based on the weight of the cosmetic composition.

Panthenol may be present in the cosmetic composition in an amount from about 0.1% to about 1%, and in some embodiments, from about 0.1% to about 0.5%, and in some embodiments, from about 0.2% to about 0.4%, and in some embodiments, from about 0.2% to about 0.25%, or any suitable combination, sub-combination, range, or sub-range thereof by weight, based on the weight of the cosmetic composition.

A hydroxy acid may be present in the cosmetic composition in an amount from about 0.25% to about 10%, and in some embodiments, from about 0.5% to about 8%, and in some embodiments, from about 1% to about 5%, and in some embodiments, from about 0.25% to about 0.5%, or any suitable combination, sub-combination, range, or sub-range thereof by weight, based on the weight of the cosmetic composition.

Carnosine may be present in the cosmetic composition in an amount from about 0.10% to about 1%, and in some embodiments, from about 0.20% to about 0.5%, and in some embodiments, from about 0.20% to about 0.25%, or any suitable combination, sub-combination, range, or sub-range thereof by weight, based on the weight of the cosmetic composition.

Thus, in various embodiments, optional active compounds, if present, are present in a cosmetic composition according to the disclosure, and each of the individual components in the ranges as described herein above, from about 0.01, 0.02, 0.03, 0.04, 0.05, 0.06, 0.07, 0.08, 0.09, 0.10, 0.20, 0.30, 0.40, 0.50, 0.60, 0.70, 0.80, 0.90, 1.0, 2, 3, 4, 5, 6, 7, 8, 9, 10, 11, 12, 13, 14, 15, 16, 17, 18, 19, 20, 21, 22, 23, 24, 25, 26, 27, 28 to about 30 percent by weight, including increments and ranges there between.

Optional Additives

The compositions can also comprise at least one additive used in the cosmetics field which does not affect the properties of the compositions according to the invention, such as, emulsifiers, emollients, fragrances, pH adjusters (citric acid, sodium chloride; neutralizing or pH-adjusting agents (e.g., triethanolamine (TEA) and sodium hydroxide), and combinations thereof), other cosmetically acceptable additives, such as but not limited to, pearlescent agents, silica, and coloring materials; essential oils; fruit extracts, for example, Pyrus Malus (Apple) Fruit Extract, and Aloe Barbadensis Leaf Juice Powder. Although the optional additives are given as examples, it will be appreciated that other optional components compatible with cosmetic applications known in the art may be used.

In accordance with the various embodiments, the amount of one or more additives, alone or in combination, present in the cosmetic composition can be present in the cosmetic composition according to the disclosure in a range from about 0.001% to about 20%, by weight, or from about 0.005% to about 0.01%, or from about 0.01% to about 0.1%, or from about 0.15% to about 5%, or from about 0.40% to about 4%, or from about 0.5% to about 2.5% by weight, or from about 1% to about 2%, or any suitable combination, sub-combination, range, or sub-range thereof by weight, based on the total weight of the composition.

Thus, any one or a combination of additives may be present, by weight, based on the total weight of the composition, each one or the combination present from about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.10, 0.20, 0.30, 0.40, 0.50, 0.60, 0.70, 0.80, 0.90, 1.0, 2, 3, 4, 5, 6, 7, 8, 9, 10, 11, 12, 13, 14, 15, 16, 17, 18, 19 to about 20 percent, by weight, based on the weight of the cosmetic composition, including increments and ranges therein and there between.

Although the optional additives are given as examples, it will be appreciated that other optional components compatible with cosmetic applications known in the art may be used that are suitable. It will be appreciated by a skilled artisan that any optional additives are present only to the extent and in amounts that do not materially adversely affect the basic and novel characteristic(s) of the claimed disclosure. Thus, in some embodiments that include optional additives, such optional additives will not materially adversely affect the solubility of the skin actives of the cosmetic composition. And in some embodiments that include optional additives, such optional additives will not materially adversely affect the cosmetic composition forming a single phase solution.

In some particular embodiments, the cosmetic composition may include optional additives, for example one or more of phenoxyethanol, terephthalylidene dicamphor sulfonic acid, trisodium ethylenediamine disuccinate, sodium citrate, sodium chloride, hydroxyacetophenone sodium benzoate, potassium sorbate, citric acid, caprylyl glycol, trisodium ethylenediamine disuccinate, or combinations thereof. In some embodiments, phenoxyethanol is present as a preservative in the cosmetic composition in a range from about 0.5% to about 2%, and in some embodiments in a range from about 1% to about 2%.

In accordance with the various embodiments, the amount of one or more actives and additives, alone or in combination, when present in the cosmetic composition according to the disclosure can be present in a range from about 0.001% to about 20%, and in some embodiments, from about 0.05% to about 0.01%, and in some embodiments, from about 0.01% to about 0.1%, and in some embodiments, from about 0.15% to about 5%, and in some embodiments, from about 0.40% to about 4%, and in some embodiments, from about 0.5% to about 2.5%, and in some embodiments, from about 0.1% to about 0.5%, and in some embodiments, from about 1% to about 2%, or any suitable combination, sub-combination, range, or sub-range thereof by weight, based on the total weight of the cosmetic composition. One of ordinary skill in the art, however, will appreciate that other ranges are within the scope of the invention.

Thus, any one or a combination of actives and additives may be present, each one or the combination present from about 0.001, 0.005, 0.01, 0.02, 0.03, 0.04, 0.05, 0.06, 0.07, 0.08, 0.09, 0.01, 0.02, 0.03, 0.04, 0.05, 0.06, 0.07, 0.08, 0.09, 0.10, 0.20, 0.30, 0.40, 0.50, 0.60, 0.70, 0.80, 0.90, 1.0, 2, 3, 4, 5, 6, 7, 8, 9, 10, 11, 12, 13, 14, 15, 16, 17, 18, 19 to about 20 percent, by weight, including increments and ranges therein and there between.

Formulations

The cosmetic composition of the present invention may be used for the production of cosmetic preparations, or dermatological preparations, more particularly topical treatment preparations, that may be formulated as single-phase or a multi-phase solution, a cosmetic serum, or aerosol, for example. Topical application to a surface may be a surface such as skin, for example.

Process of Making Stabilized Composition with Ascorbic Acid and without Oil:

The disclosure provides a composition that is stable. As used herein, stable means and includes: Physical stability, wherein, over a predetermined time, the actives remain solubilized in solution and do not crystallize out, such phase stability evidenced by the absence of visually discernable crystal formation or by direct chemical measurement of solubilized active, or both; and Phase stability, wherein the cosmetic composition remains as a single phase, clear solution, that does not separate into more than one layer, or become cloudy (which could be evidence of chemical breakdown of one or more actives), such physical stability evidenced by visual inspection. For purposes hereof, a composition that demonstrates physical stability and does not become cloudy, as evidenced by visual inspection, is presumed to be chemically stable, such that the actives remain soluble and do not decompose or chemically react to form non-active compounds in a manner that would diminish or eliminate their capability of acting according to their intended function at that time of application. As disclosed and exemplified herein, an inventive composition remains chemically stable (wherein actives do not precipitate, decompose or react as evidenced by one or more of crystal formation, measured loss of solubility, and/or the cosmetic composition becomes cloudy), at temperatures in the range from about 5° C. to about 45° C. and at a pH that is in the range from about 3.0 to about 3.5, all over a time period up to at least about 4 days or more, or up to at least about 8 days, or up to at least about 10 days, or for a period of more than 4 days, or for a period of more than 8 days, or for a period of more than 10 days.

Compositions according to the disclosure are made using the following procedures: water, solvents, and actives other than ascorbic acid and sodium hyaluronate are stirred together until dissolved to a clear solution. Sodium hyaluronate is sprinkled on the surface of the solution without stirring and the mixture allowed to form a gel without stirring for about 3 hours. After the three-hour period, the gel is stirred to obtain a uniform viscous solution. The solution is degassed under vacuum and saturated with an inert gas such as argon or nitrogen. This degassing and saturating procedure was carried out three times. Ascorbic acid is added with stirring, the solution is again degassed under vacuum and saturated with an inert gas, and then stirred for 30 to 45 minutes to yield a clear solution which is then degassed and saturated with an inert gas.

Process of Making Stabilized Composition with Ascorbic Acid and oil, for example, tocopherol: A further embodiment of the present invention is a product made by a process described herein. Compositions having increased a hydrophobic component such as tocopherol are made by mixing water, actives other than ascorbic acid, tocopherol and sodium hyaluronate until a clear solution is formed. Sodium hyaluronate is sprinkled on the surface of the solution and allowed to dissolve for about three hours to form a first solution. Separately, a mixture that includes solvents, surfactant, an optional additive preservative, for example, phenoxyethanol, and the hydrophobic component is gently heated with stirring to 60° C. to form a second solution. This second solution is then added to the first solution with stirring until the combined solution is clear. Cooling of the second solution is not required. The combined solution is degassed under vacuum with an inert gas such as saturated argon or nitrogen. The degassing and saturating is carried out three times. Ascorbic acid is added with stirring. The final solution is degassed and saturated with the inert gas and stirred to form a clear solution.

Methods of Use of Stabilized Ascorbic Acid Compositions: The present disclosure also provides a method of treating a condition of a subject that results from radical damage comprising administering a composition of the present invention to the subject. Treating, as used herein, means prophylactic and/or therapeutic treatment of a subject. "Prophylactic" treatment is a treatment administered to a subject who does not have symptoms of radical-induced damage or has early signs of such damage or anticipates being exposed to situations having risk of radical-induced damage. "Therapeutic" treatment is a treatment administered to a subject who has signs of radical-induced damage.

Such a condition may be photo-aging, or diseases or disorders of the skin such as, for example, skin cancer, skin irritation or inflammation, dermatitis, allergy, psoriasis, acne, eczema, rosacea, or radiation exposure.

The examples below according to the invention are given by way of illustration and without a limiting nature. The names are the chemical name or the INCI name. The amounts of active ingredients are given therein as % by weight based on raw material compositions comprising 100% of the listed ingredient, unless otherwise mentioned.

EXAMPLES

Example 1: Compositions

Various representative embodiments of the inventive compositions are exemplified herein.

TABLE 1

Compositions

| | Comparative Compositions | | Inventive Compositions | |
|---|---|---|---|---|
| INCI UE | Comp 1 | Comp 1 | Inv 1 | Inv 2 |
| SODIUM HYALURONATE | 0.07 | 0.07 | 0.07 | 0.07 |
| WATER | 50.98 | 49.98 | 44.98 | 43.98 |
| HEXYLENE GLYCOL | 9.29 | 9.29 | 9.29 | 9.29 |
| LAURETH-23 | 3.0 | 3.0 | 3.0 | 3.0 |
| DIPROPYLENE GLYCOL | 15.71 | 15.71 | 15.71 | 15.71 |
| TOCOPHEROL | 1.0 | 1.0 | 1.0 | 1.0 |
| PHENOXYETHANOL | 1.0 | 1.0 | 1.0 | 1.0 |
| FERULIC ACID | 0.5 | 0.5 | 0.5 | 0.5 |
| CHLOROGENIC ACIDS | 1.2 | 1.2 | 1.2 | 1.2 |
| ASCORBIC ACID | 15.0 | 15.0 | 15.0 | 15.0 |
| PANTHENOL | 0.25 | 0.25 | 0.25 | 0.25 |
| PHYTIC ACID* | 2.0* | 2.0* | 2.0* | 2.0* |
| SODIUM HYDROXIDE | 0.0 | 0.0 | 0.0 | 0.0 |
| SODIUM DILAURAMIDOGLUTAMIDE LYSINE | | 1.0 | | 1.0 |
| TEREPHTHALYLIDENE DICAMPHOR SULFONIC ACID** | | | 6.0** | 6.0** |

*Phytic Acid raw material = 50% phytic acid in carrier
**Terephthalylidene Dicamphor Sulfonic Acid (MSX) raw material = 33% active in carrier Example 2: Evaluation of Antioxidant UV Photostability Inventive and comparative compositions were evaluated for photostability of ascorbic acid and ferulic acid after an exposure of about 5 J/cm$^2$, at a UVA flow of about 0.0037 W/cm$^2$ for a period of time in a range from about 30 minutes to about 60 minutes, representing classical urban daily UV exposure, mainly indoor. The objective of the analysis is to study the effect of the radiation on antioxidant stability with and without a UV filter stabilizer (terephthalylidene dicamphor sulfonic acid) in the presence of the surfactant sodium dilauramidoglutamide lysine (Pellicier). Results are shown in Table 2, below. The results reflect the residual fraction (as a percentage of the original amount) of the antioxidants, ferulic acid and ascorbic acid, obtained after UV exposure with a standard deviation (RDS) of +/−6% in absolute value, related to the technical implementation.

TABLE 2

| Composition Tested | Residual Ascorbic Acid (%) | Residual Ferulic Acid (%) |
|---|---|---|
| Comparative 1 | 96 | 40 |
| Comparative 2 | 98 | 40 |
| Inventive 1 | 88 | 55 |
| Inventive 2 | 83 | 53 |

The results show that addition of the UV filter stabilizer confers improved ferulic acid chemical stability when exposed to classical urban daily exposure to UV radiation as compared with controls lacking the UVA filter stabilizer. Generally, stabilization of ferulic acid by the UVA filter after classical urban daily exposure to UV radiation (as compared with controls lacking the UVA filter stabilizer) is from about 50% and up to about 55%. More generally, stabilization is exhibited by preservation of at least 50% of the antioxidant active after classical urban daily exposure to UV radiation. It is noted that while both ferulic acid and Vitamin C are known to be sensitive to UV radiation, the data show that the UVA filter stabilizer protected ferulic acid but not Vitamin C, a result that is unexpected both in regard to the observed protection of ferulic acid and in regard to the fact that Vitamin C was not similarly protected.

While the disclosure has been described with reference to described embodiments, it will be understood by those skilled in the art that various changes may be made and equivalents may be substituted for elements thereof without departing from the scope of the disclosure. In addition, many modifications may be made to adapt a particular situation or material to the teachings of the disclosure without departing from the essential scope thereof. Therefore, it is intended that the disclosure is not limited to the particular embodiment disclosed as the best mode contemplated for carrying out this disclosure, but that the disclosure will include all embodiments falling within the scope of the appended claims.

"At least one," as used herein, means one or more and thus includes individual components as well as mixtures/combinations.

The transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinarily associated with the specified material(s). The term "consisting essentially of" limits the scope of a claim to the specified elements, steps or material(s) and those that do not materially affect the basic and novel characteristic(s) of the claimed disclosure. All materials and methods described herein that embody the present disclosure can, in alternate embodiments, be more specifically defined by any of the transitional terms "comprising," "consisting essentially of," and "consisting of."

The terms "free" and "devoid" indicates that no reliably measurable excluded material is present in the cosmetic composition, typically 0% by weight, based on the total weight of the cosmetic composition. The term "essentially free" means that, while it prefers that no excluded material is present in the cosmetic composition, it is possible to have very small amounts of the excluded material in the cosmetic composition of the invention, provided that these amounts do not materially affect the advantageous properties of the cosmetic composition. In particular, "essentially free" means that excluded material can be present in the cosmetic composition at an amount of less than about 0.1% by weight, based on the total weight of the cosmetic composition.

Other than in the operating examples, or where otherwise indicated, all numbers expressing quantities of ingredients and/or reaction conditions are to be understood as being modified in all instances by the term "about," meaning within 10% of the indicated number (e.g. "about 10%" means 9%-11% and "about 2%" means 1.8%-2.2%).

All percentages and ratios are calculated by weight unless otherwise indicated. All percentages are calculated based on the total composition unless otherwise indicated. Generally, unless otherwise expressly stated herein, "weight" or "amount" as used herein with respect to the percent amount of an ingredient refers to the amount of the raw material comprising the ingredient, wherein the raw material may be described herein to comprise less than and up to 100% activity of the ingredient. Therefore, percent, by weight, based on the weight of the cosmetic composition, of an active in a composition is represented as the amount of raw material containing the active that is used, and may or may not reflect the final percentage of the active, wherein the final percentage of the active is dependent on the percent, by weight, based on the weight of the cosmetic composition, of active in the raw material.

The terms "percent, by weight, based on the weight of the cosmetic composition," and "wt %" may be used interchangeably and mean percent by weight, based on the total weight of a composition, article or material, except as may be specified with respect to, for example, a phase, or a system that is a component of a composition, article or material. All ranges and amounts given herein are intended to include subranges and amounts using any disclosed point as an end point. Thus, a range of "1% to 10%, such as 2% to 8%, such as 3% to 5%," is intended to encompass ranges of "1% to 8%," "1% to 5%," "2% to 10%," and so on. All numbers, amounts, ranges, etc., are intended to be modified by the term "about," whether or not so expressly stated. Similarly, a range given of "about 1% to 10%" is intended to have the term "about" modifying both the 1% and the 10% endpoints. Further, it is understood that when an amount of a component is given, it is intended to signify the amount of the active material unless otherwise specifically stated.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements. The example that follows serves to illustrate embodiments of the present disclosure without, however, being limiting in nature.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

What is claimed is:

1. A cosmetic composition comprising:
an organic UVA filter-stabilized antioxidant formulation comprising:
a combination of at least one hydroxycinnamate derivative; and
at least one organic, water-soluble UVA filter comprising terephthalylidene dicamphor sulfonic acid; and
a carrier formulation comprising a water phase,
wherein the cosmetic composition demonstrates stabilization from decomposition of the at least one hydroxycinnamate derivative after UV exposure as compared with controls lacking the UVA filter stabilizer, and
wherein the cosmetic composition is free of titanium dioxide.

2. The cosmetic composition according to claim 1, wherein at least one hydroxycinnamate derivative includes ferulic acid.

3. The cosmetic composition according to claim 1, wherein the cosmetic composition demonstrates stabilization of the hydroxycinnamate derivative after classical urban daily exposure to UV radiation as compared with controls lacking the UVA filter stabilizer from about 50% or more, wherein classical urban daily exposure to UV radiation is exposure of about 5 J/cm$^2$, at a UVA flow of about 0.0037 W/cm$^2$ for a period of time in a range from about 30 minutes to about 60 minutes.

4. The cosmetic composition according to claim 1, wherein the at least one hydroxycinnamate derivative is present in the cosmetic composition in a range from about 0.1% to about 5%, by weight, based on the weight of the composition.

5. The cosmetic composition according to claim 1, wherein the at least one hydroxycinnamate derivative is ferulic acid.

6. The cosmetic composition according to claim 1, wherein the composition further includes ascorbic acid present in the cosmetic composition in a range from about 5% to about 30%, by weight, based on the weight of the composition, the ascorbic acid present in a ratio of water to ascorbic acid in a range from about 3:1 to about 10:1, based on the weight of the cosmetic composition.

7. The cosmetic composition according to claim 1, wherein the at least one organic, water-soluble UVA filter is present in the cosmetic composition in a range from about 0.4% to about 10%, by weight, based on the weight of the composition.

8. The cosmetic composition according to claim 1, wherein the at least one organic, water-soluble UVA filter consists of the terephthalylidene dicamphor sulfonic acid.

9. The cosmetic composition according to claim 1, wherein the cosmetic composition comprises one or a combination of phytic acid or chlorogenic acid, wherein phytic acid, when present in the cosmetic composition, is present in a range from about 0.25% to about 10%, and wherein chlorogenic acid, when present in the cosmetic composition, is present in a range from about 0.5% to about 1.5%, each by weight, based on the weight of the composition.

10. The cosmetic composition according to claim 1, wherein the cosmetic composition comprises one or a combination of additional ingredients selected from the group consisting of hexylene glycol present in the composition from about 5% to about 25%, dipropylene glycol present in the composition from about 5% to about 25%, laureth-23 present in the composition from about 1% to about 5%, sodium dilauramidoglutamide lysine present in the composition from about 1% to about 5%, each by weight, based on the weight of the composition.

11. The cosmetic composition according to claim 1, wherein the cosmetic composition is a single phase solution comprising the water phase, a multi-phase solution wherein the water phase is one of at least one water phase, a water-in-oil emulsion comprising the water phase, an oil-in-water emulsion comprising the water phase, or a silicone-in-water emulsion comprising the water phase.

12. The cosmetic composition according to claim 1, wherein the cosmetic composition is provided in a product form for application to keratinous tissue selected from the group consisting of a hydroglycolic solution, a micellar water, a cream, a lotion, a toner, a cleanser, or a make-up remover, and wherein the cosmetic composition is either a leave-on or a rinse-off formulation.

13. The cosmetic composition according to claim 1, wherein the cosmetic composition comprises one or a combination of active compounds selected from the group consisting of tocopherol, panthenol and hyaluronic acid.

14. A cosmetic composition comprising:
(a) an organic UVA filter-stabilized antioxidant formulation comprising:
i. at least one hydroxycinnamate derivative present in the cosmetic composition in a range from about 0.1% to about 5%, by weight, based on the weight of the composition; and
ii. at least one organic water-soluble UVA filter; and
(b) a carrier formulation comprising: a water phase, and one or more additional components comprising a glycol, a humectant, a preservative, a surfactant, a thickener, an active compound, an emulsifier, an emollient, or a combination thereof,
wherein the cosmetic composition is free of titanium dioxide.

15. The cosmetic composition according to claim 14, wherein the cosmetic composition demonstrates stabilization of the hydroxycinnamate derivative after classical urban daily exposure to UV radiation as compared with controls lacking the UVA filter stabilizer from about 50% and up to about 55%, wherein classical urban daily exposure to UV radiation is exposure of about 5 J/cm$^2$, at a UVA flow of about 0.0037 W/cm$^2$ for a period of time in a range from about 30 minutes to about 60 minutes.

16. The cosmetic composition according to claim 14, wherein the at least one hydroxycinnamate derivative is present in a range from about 0.2% to about 5%, the ascorbic acid is present in a range from about 5% to about 30%, the at least one organic water-soluble UVA filter is present in a range from about 0.4% to about 10%, all amounts by weight, based on the weight of the composition.

17. The cosmetic composition according to claim 14, further comprising one of phytic acid present in a range from about 0.25% to about 10% or chlorogenic acid present in a range from about 0.25% to about 10%, or a combination thereof, all amounts by weight, based on the weight of the composition.

18. The cosmetic composition according to claim 14, wherein the carrier formulation comprises one or a combination of additional ingredients selected from the group consisting of hexylene glycol, dipropylene glycol, laureth-23, sodium dilauramidoglutamide lysine and sodium hydroxide, and one or a combination of active compounds selected from the group consisting of tocopherol, panthenol and hyaluronic acid.

19. A cosmetic composition comprising:
(a) an organic UVA filter-stabilized antioxidant formulation comprising:
   i. ferulic acid present in a range from about 0.2% to about 5%;
   ii. ascorbic acid present in a range from about 0% to about 30%;
   iii. terephthalylidene dicamphor sulfonic acid present in a range from about 0.4% to about 10%;
   iv. phytic acid present in a range from about 0.25% to about 10% and chlorogenic acid present in a range from about 0.25% to about 10%;
   all amounts by weight, based on the weight of the composition; and
(b) a carrier formulation comprising a water phase and one or a combination of additional ingredients selected from the group consisting of hexylene glycol, dipropylene glycol, laureth-23, sodium dilauramidoglutamide lysine and sodium hydroxide, and one or a combination of active compounds selected from the group consisting of tocopherol, panthenol and hyaluronic acid
wherein the cosmetic composition demonstrates stabilization of the ferulic acid after classical urban daily exposure to UV radiation as compared with controls lacking the terephthalylidene dicamphor sulfonic acid from about 50% and up to about 55%, wherein classical urban daily exposure to UV radiation is exposure of about 5 $J/cm^2$, at a UVA flow of about 0.0037 $W/cm^2$ for a period of time in a range from about 30 minutes to about 60 minutes.

20. The cosmetic composition according to claim 19, wherein ascorbic acid is present in the cosmetic composition in a range from about 5% to about 30%, by weight, based on the weight of the composition, the ascorbic acid present in a ratio of water to ascorbic acid in a range from about 3:1 to about 10:1, based on the weight of the cosmetic composition.

* * * * *